(12) United States Patent
Fujikura

(10) Patent No.: US 7,591,782 B2
(45) Date of Patent: Sep. 22, 2009

(54) BALLOON ATTACHING JIG OF ENDOSCOPE

(75) Inventor: Tetsuya Fujikura, Saitama (JP)

(73) Assignees: Fujinon Corporation, Tochigi (JP); SRJ Corporation, Tochigi (JP)

( * ) Notice: Subject to any disclaimer, the term of this patent is extended or adjusted under 35 U.S.C. 154(b) by 315 days.

(21) Appl. No.: 11/004,866

(22) Filed: Dec. 7, 2004

(65) Prior Publication Data

US 2005/0125005 A1    Jun. 9, 2005

(30) Foreign Application Priority Data

Dec. 8, 2003    (JP)    ............... 2003-408845
Nov. 5, 2004    (JP)    ............... 2004-322792

(51) Int. Cl.
*A61B 1/00*    (2006.01)
(52) U.S. Cl. ............... 600/116; 600/115; 600/124
(58) Field of Classification Search ............... 600/115, 600/124, 116; 29/450; 128/898
See application file for complete search history.

(56) References Cited

U.S. PATENT DOCUMENTS

| | | | | |
|---|---|---|---|---|
| 2,038,840 | A | * | 4/1936 | Hall ............... 29/235 |
| 5,222,970 | A | * | 6/1993 | Reeves ............... 606/195 |
| 5,391,178 | A | | 2/1995 | Yapor |
| 5,779,672 | A | * | 7/1998 | Dormandy, Jr. ............ 604/99.04 |
| 6,049,960 | A | * | 4/2000 | Pilling et al. ............... 29/450 |
| 6,338,717 | B1 | * | 1/2002 | Ouchi ............... 600/462 |
| 2003/0004434 | A1 | * | 1/2003 | Greco et al. ............... 600/561 |

FOREIGN PATENT DOCUMENTS

| | | | |
|---|---|---|---|
| JP | 5-15487 A | | 1/1993 |
| JP | 8-847775 A | | 4/1996 |
| JP | 08084775 A | * | 4/1996 |
| JP | 9-308605 A | | 12/1997 |
| JP | 2005-137413 A | | 6/2005 |

OTHER PUBLICATIONS

European Search Report issued Mar. 3, 2005.
Japanese Office Action and English translation thereof as issued on Dec. 16, 2005.

* cited by examiner

*Primary Examiner*—John P Leubecker
*Assistant Examiner*—Victoria W Chen
(74) *Attorney, Agent, or Firm*—Harness, Dickey & Pierce (57) ABSTRACT

A balloon attaching jig is constituted by a ring member and a pair of nail members. After the insertion of the pair of nail members into an attaching hole of a balloon, the leading end of an insertion portion of an endoscope is pushed into an opening of the ring member. The diameter of the pair of nail members is expanded by a pushing-in force of the leading end of the insertion portion generated during this pushing in. As a result of this, the leading end of the insertion portion is inserted into the attaching hole of the balloon and hence the balloon can be easily attached to the leading end of the insertion portion of the endoscope.

6 Claims, 11 Drawing Sheets

BALLOON ATTACHING JIG OF ENDOSCOPE

BACKGROUND OF THE INVENTION

1. Field of the Invention

The present invention relates to a balloon attaching jig of an endoscope and, more particularly, to a balloon attaching jig of an endoscope that is used to attach a balloon to an insertion portion of the endoscope or an insertion aid that provide a guide in inserting the insertion portion into a body cavity.

2. Description of the Related Art

In recent years, endoscope apparatuses in which a balloon is mounted on an outer peripheral surface of an insertion portion of an endoscope or a balloon is mounted on an outer peripheral surface of an insertion aid that provides a guide in inserting the insertion portion into a body cavity have been developed. In these endoscope apparatuses, because the insertion portion or the insertion aid can be fixed in a body cavity by inflating the balloon, the leading end of the insertion portion can be fixed in a desired direction. The above-described balloon is formed in roughly barreled shape, and the insertion portion or the insertion aid can be fixed in an inserted condition. Therefore, in attaching the balloon, it is necessary that the insertion portion or the insertion aid be inserted, with an opening for balloon insertion kept expanded.

The Japanese Patent Application Publication No. 5-15487 describes a method by which a balloon is attached to an inner circumferential surface of a barrel body by being adsorbed thereon. According to this method, because the inside diameter of the balloon can be expanded by causing the balloon to be adsorbed on the inner circumferential surface of the barrel body, it is possible to insert the insertion portion or the insertion aid. However, this method had the problem that a dedicated suction device is necessary.

The Japanese Patent Application Publication No. 9-308605 describes a method by which a barrel-shaped curved rubber is attached by use of the main body of a tubular mounting fixture and a fastener screwed into the base end of the mounting fixture main body. The diameter of the leading end of the mounting fixture main body is reduced by fastening the fastener. Therefore, by loosening the fastener thereby to increase the diameter of the leading end of the mounting fixture main body, the inside diameter of the curved rubber can be expanded and it is possible to cause the insertion portion to be inserted.

SUMMARY OF THE INVENTION

However, the method described in the Japanese Patent Application Publication No. 9-308605 had the problem that the mounting work itself cannot be simplified because it is necessary to add the work of screwing the fastener into the mounting fixture main body and loosening the fastener.

Also, in the method described in the Japanese Patent Application Publication No. 9-308605, the diameter of the leading end of the mounting fixture main body decreases when the fastener is screwed into the mounting fixture main body, whereas the diameter of the base end of the mounting fixture main body remains to be large. This posed the problem that the work of putting the curved rubber on the mounting fixture main body takes a lot of time and is troublesome. There was also a possibility that the curved rubber put on the base end side might be excessively expanded, resulting in damage to the curved rubber.

The present invention was made in view of these circumstances and has as its object the provision of a balloon attaching jig of an endoscope that can easily attach a balloon to an insertion portion of an endoscope or an insertion aid.

To achieve the above-described object, in the first aspect of the invention there is provided a balloon attaching jig of an endoscope that is used to attach a balloon to an insertion portion of an endoscope or an insertion aid that aids in insertion of the insertion portion into a body cavity by inserting the insertion portion or the insertion aid into an attaching hole of the balloon, comprising a guide portion that is inserted into the attaching hole of the balloon and into which the insertion portion or the insertion aid is inserted, wherein the diameter of the guide portion can expand and contract freely.

To achieve the above-described object, in the second aspect of the invention there is provided a balloon attaching jig of an endoscope that is used to attach a balloon to an insertion portion of an endoscope or an insertion aid that aids in insertion of the insertion portion into a body cavity by inserting the insertion portion or the insertion aid into an attaching hole of the balloon, which comprises: a ring member having an inside diameter larger than the outside diameter of the insertion portion or the insertion aid, and a plurality of guide pieces that are formed integrally with the ring member or have a base end fixed to the ring member. In this balloon attaching jig, in a state that the guide pieces are inserted into an attaching hole of the balloon, when the insertion portion of the endoscope or the insertion aid is pushed into an opening of the ring member, a diameter formed by the guide pieces is expanded by a pushing-in force generated by pushing-in so that the insertion portion of the endoscope or the insertion aid is inserted into the attaching hole of the balloon.

According to the second aspect, the guide pieces of the balloon attaching jig are inserted into an attaching hole of a balloon. At this time, the guide pieces themselves do not have an elastic force large enough to expand the diameter of the attaching hole of the balloon. Therefore, in this state, an inside diameter for insertion formed by the multiple guide pieces is small than the outside diameter of the insertion portion or the insertion aid. In this state, the leading end of the insertion portion or the insertion aid is pushed in from the ring member of the balloon attaching jig and a stronger pushing-in force than before is given to the insertion portion or the insertion aid at a point of time when the leading end of the insertion portion or the insertion aid has come into contact with the multiple guide pieces. The multiple guide pieces are expanded by this pushing-in force so as to expand the diameter thereof and the insertion portion of the endoscope or the insertion aid becomes inserted into the attaching hole of the balloon. As a result of this, the balloon can be easily attached to the insertion portion of the endoscope or the insertion aid.

According to the third aspect of the invention, the balloon attaching jig is made of a tearable material, such as paper and resin film. After the mounting of a balloon on the insertion portion of the endoscope or the insertion aid, the balloon attaching jig is removed from the insertion portion or the insertion aid. In this case, if the balloon attaching jig is made of a material incapable of being torn, after the removal of the guide pieces from the attaching hole of the balloon, this balloon attaching jig must be withdrawn from the insertion portion or the insertion aid by causing the balloon attaching jig to pass by the outer peripheral part of the balloon. If the balloon attaching jig is caught by the balloon during this withdrawal, the balloon made of a thin rubber sheet may sometimes be broken. In contrast, in the second aspect of the invention, after the removal of the guide pieces from the attaching hole of the balloon, the balloon attaching jig is removed from the insertion portion or the insertion aid by being torn. As a result of this, it becomes unnecessary to cause the balloon attaching jig to pass by the outer peripheral part of the balloon and, therefore, it is possible to prevent the balloon from being broken by the balloon attaching jig.

According to the fourth aspect of the invention, a cut is formed into the balloon attaching jig from an end of a tubular body. By forming a cut in the balloon attaching jig from an end of a tubular body, it is possible to easily tear the balloon attaching jig.

To achieve the above-described object, in the fifth aspect of the invention there is provided a balloon attaching jig of an endoscope that is used to attach a balloon to an insertion portion of an endoscope or an insertion aid that aids in insertion of the insertion portion into a body cavity by inserting the insertion portion or the insertion aid into an attaching hole of the balloon, which comprises: a ring member having an inside diameter larger than the outside diameter of the insertion portion or the insertion aid, and a plurality of guide pieces that have a base end fixed to the ring member, wherein at least one of the ring member and the guide pieces is formed from an elastic member having a larger restoring force than the balloon. In this balloon attaching jig, when the guide pieces are inserted into the attaching hole of the balloon while the elastic member is being elastically deformed, the elastic member expands the attaching hole of the balloon from inside by the restoring force.

According to the fifth aspect, because at least one of the ring member and the guide pieces is formed from an elastic member, by elastically deforming the elastic member, the leading ends of the multiple guide pieces can be caused to close to each other and it is possible to easily insert the leading ends into the attaching hole of the balloon. Also, by causing the elastic member to be restored, the attaching hole of the balloon can be expanded from inside. Therefore, the insertion portion or the insertion aid can be easily inserted into the attaching hole of the balloon.

According to a balloon attaching jig of an endoscope related to the invention, the balloon attaching jig is constituted by a ring member and multiple guide pieces, the multiple guide pieces are inserted into an attaching hole of the balloon, and the insertion portion or the insertion aid can be inserted into the attaching hole of the balloon by a pushing-in force that is generated when the insertion portion of the endoscope or the insertion aid is pushed into an opening of the ring member while the diameter of the multiple guide pieces is being expanded. Therefore, the balloon can be easily attached to the insertion portion of the endoscope or the insertion aid.

Also, according to a balloon attaching jig of an endoscope related to the invention, the leading ends of the guide pieces can be easily inserted into the attaching hole of the balloon by elastically deforming at least one of the ring member and the guide pieces, and the attaching hole of the balloon can be expanded from inside by causing the deformed ring member or guide pieces to be restored. Therefore, the insertion portion or the insertion aid can be easily inserted into the attaching hole of the balloon and the balloon mounting work can be easily performed.

DETAILED DESCRIPTION OF THE PREFERRED EMBODIMENTS

Preferred embodiments of a balloon attaching jig of an endoscope related to the invention will be described below with reference to the accompanying drawings.

Figure 1:
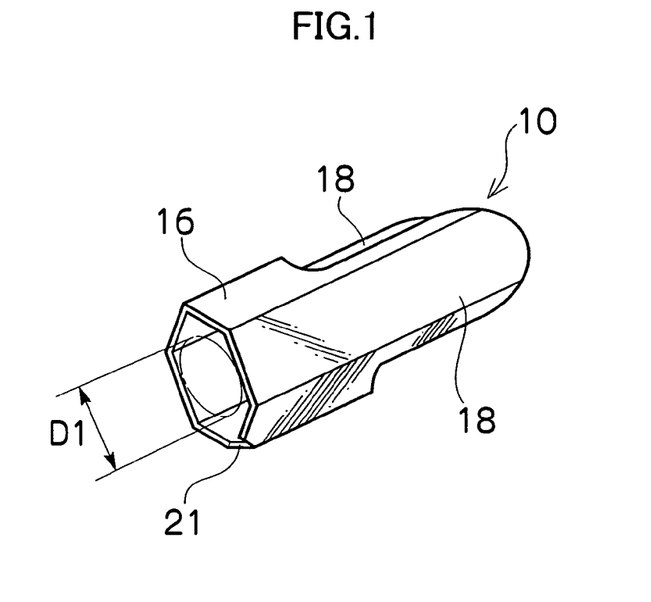
FIG. 1 is a perspective view of a balloon attaching jig of an endoscope in an embodiment of the invention.
Figure 2:
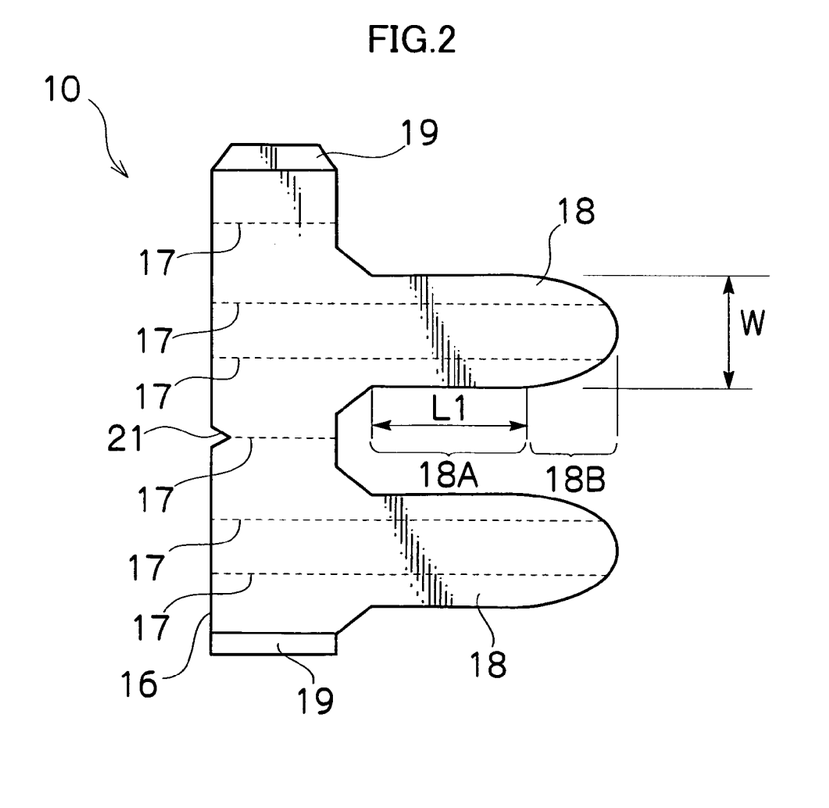
FIG. 2 is a developed view of the balloon attaching jig shown in FIG. 1.
Figure 3:
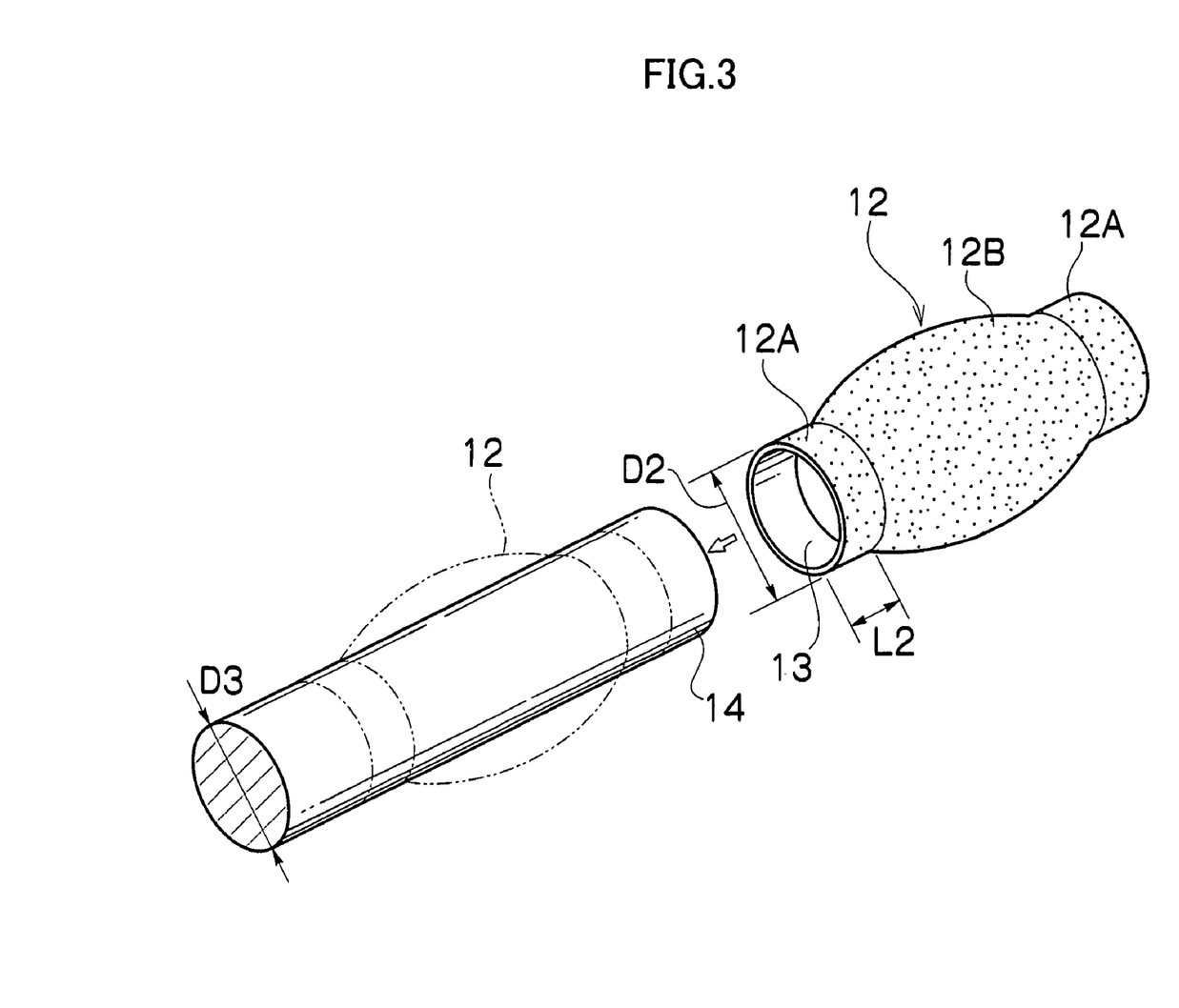
FIG. 3 is a perspective view of a balloon mounted to the leading end of an insertion portion of an endoscope by use of the balloon attaching jig shown in FIG. 1 and the leading end of the insertion portion.

FIG. 1 is a perspective view of a balloon attaching jig 10 in an embodiment of the invention and FIG. 2 is a developed view of the balloon attaching jig 10 of FIG. 1. FIG. 3 is a perspective view of a balloon 12 mounted to the leading end 14 of an insertion portion of an endoscope by use of the balloon attaching jig shown in FIG. 1. Incidentally, in the following embodiments, descriptions will be given of a case where the balloon 12 is attached to the leading end 14 of an insertion portion. However, the invention is not limited to this case and the insertion portion may be attached to an insertion aid for insertion into a body cavity.

As shown in FIG. 3, the balloon 12 is formed in roughly barreled shape as a whole, with both ends being necked, and the balloon 12 is constituted by cylindrical fixing parts 12A at both ends and an inflation part 12B in the middle. The balloon 12 is an elastic body such as rubber, and formed in such a manner that the inside diameter D2 of an attaching hole 13 of the fixing part 12A is smaller than the outside diameter D3 of the leading end of the insertion portion 14. Therefore, as indicated by the alternate long and two short dashes lines of FIG. 3, when the leading end of the insertion portion 14 is inserted into the balloon 12, the fixing parts 12A of the balloon 12 come into close contact, due to the elastic force thereof, with the outer peripheral surface of the leading end of the insertion portion 14. By winding a thread around the fixing pats 12A or inserting a fixing ring into the fixing pats 12A, the balloon 12 is firmly mounted on the leading end of the insertion portion 14. When air is supplied to the interior of the mounted balloon 12, the inflation part 12B inflates and by sucking the air in the interior, the inflation part 2B shrinks and comes into close contact with the outer peripheral surface of the leading end of the insertion portion 14. Incidentally, the shape of the balloon 12 is not limited to the above-described example, and for example, a cylindrical balloon or a balloon having only one fixing part 12A may be used.

The balloon attaching jig 10 shown in FIG. 1 is a mounting fixture to put the balloon 12 on the leading end of the insertion portion 14 and is integrally constituted by a ring member 16 and a pair of nail members (a guide portion, multiple guide pieces) 18. This balloon attaching jig 10 is formed in the shape of a hexagonal tube by being mountain folded along six mountain folding lines 17 as shown in FIG. 2, and the balloon attaching jig 10 shown in FIG. 1 is assembled by bonding together overlap width parts 19 formed on both ends of a sheet that forms the ring member 16. Incidentally, although in this embodiment the ring member 16 and the pair of nail members 18 are formed as one body, the ring member 16 and the pair of finger members 18 may be separately formed and may be bonded together with an adhesive.

The ring member 16 is formed in such a manner that the inside diameter D1 thereof is a little larger than the outside diameter D3 of the leading end of the insertion portion 14 of FIG. 3 and the leading end of the insertion portion 14 can be inserted into the ring member 16. The balloon attaching jig 10 is made of tearable paper. Furthermore, in order to facilitate the tearing, as shown in FIG. 2, a cut 21 is formed along a somewhat short mountain folding line 17. Incidentally, the material for the balloon attaching jig 10 is not limited to paper, and materials capable of being torn such as resin film can be used.

The pair of nail members 18 is formed at an interval of 180 degrees around the ring member 16 so as to be opposed to each other when the balloon attaching jig 10 is assembled. The pair of nail members 18 is constituted by a rectangular guide portion 18A formed with a constant width W as shown in FIG. 2 and a plug portion 18B formed on the leading end side of the guide portion 18A.

The guide portion 18A is formed in such a manner that the width W thereof is larger than the outside diameter D3 of the leading end of the insertion portion (see FIG. 3) 14 and the length L1 thereof is larger than the length L2 of the fixing part 12A of the balloon 12 (see FIG. 3). On the other hand, the plug portion 18B is formed in the shape of a tongue with a rounded tip and this shape is such that the tongue part 18B can be easily inserted into the attaching hole 13 of the fixing part 12A of the balloon 12 without damaging the balloon 12.

Next, a method of attaching the balloon 12 by use of the balloon attaching jig 10 constructed as described above will be described below with reference to FIGS. 4A to 4D.

Figure 4A:
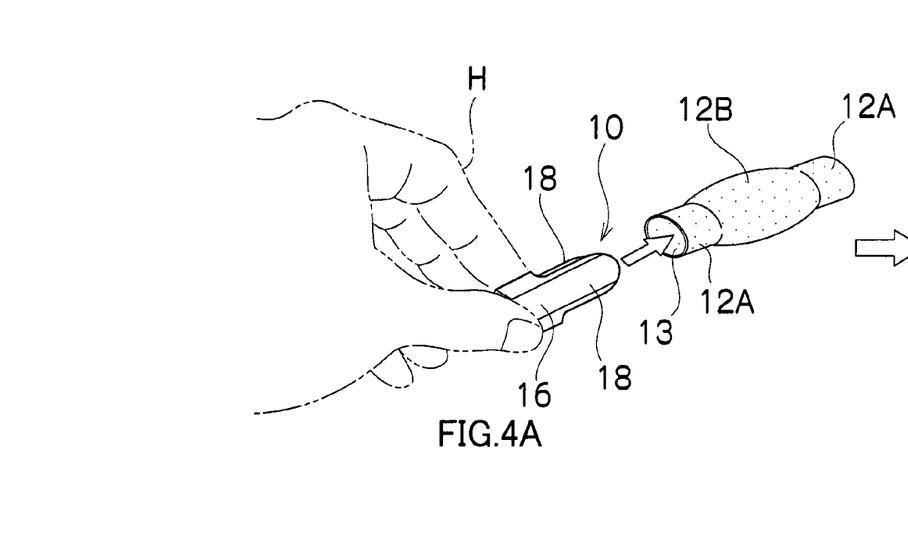
FIGS. 4A, 4B, 4C, and 4D are each an explanatory drawing that shows procedures for attaching a balloon to the leading end of the insertion portion by use of the balloon attaching jig shown in FIG. 1.
Figure 4B:
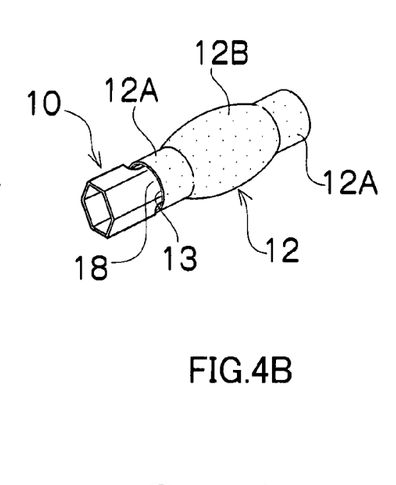

First, as shown in FIG. 4A, the operator picks up the ring member 16 of the balloon attaching jig 10 in a folded condition with the thumb and forefinger of one hand H, as shown in FIG. 4B, inserts the plug portion 18B of the nail member 18 into the attaching hole 13 of the fixing part 12A of the balloon 12, and pushes the nail member 18 into the attaching hole 13 until the full length of the guide portion 18A is inserted into the attaching hole 13. Next, the operator depresses the acute-angle corners of the ring member 16 with the thumb and forefinger from both outsides. As a result of this, the ring member 16 expands from the folded condition (with the attaching hole in a flat condition) to form a hexagonal balloon attaching jig 10 as shown in FIG. 1.

As a result of the insertion of the plug portion 18B into the attaching hole 13, the balloon attaching jig 10 is mounted in the attaching hole 13 of the balloon 12. Incidentally, at this time, the pair of nail members 18 has no elastic force large enough to expand the diameter of the attaching hole 13 of the balloon 12. Therefore, at the stage at which the balloon attaching jig 10 has been mounted in the balloon 12, the inside diameter for insertion formed by the pair of nail members 18 is smaller than the outside diameter D3 of the leading end of the insertion portion 14.

In this state, the operator picks up again the ring member 16 of the balloon attaching jig 10 with the thumb and forefinger and again deforms the ring member 16 into the shape of a hexagonal tube against the elastic force of the fixing part 12A. As a result of this, the insertion of the leading end of the insertion portion 14 into the ring member 16 becomes possible.

Subsequently, the operator grips the insertion portion with the other hand, inserts the leading end of the insertion portion 14 into the hexagonal opening of the ring member 16 and pushes in the leading end of the insertion portion 14.

When the leading end of the insertion portion 14 is pushed in, the leading end of the insertion portion 14 comes into contact with the guide portions 18A of the pair of nail members 18, 18 that is closed by the elastic force of the fixing part 12A and receives the resistance of insertion. At this time, a stronger pushing-in force than before is given to the leading end of the insertion portion 14.

Figure 4C:
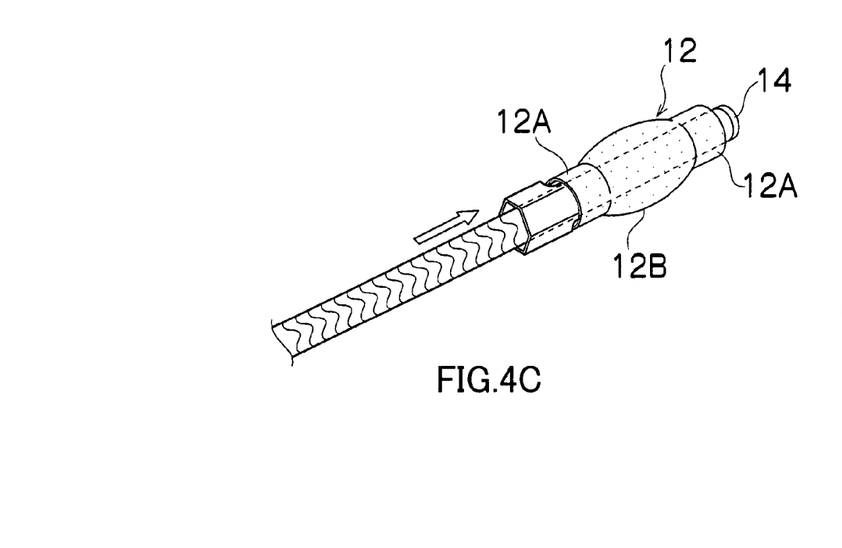

The guide portions 18A of the pair of nail members 18 are expanded by this pushing-in force so as to expand the diameter thereof, with the result of that the inside diameter for insertion is expanded and the leading end of the insertion portion 14 is inserted into the attaching hole 13 of the fixing part 12A, with the guide members 18A serving as guides. And when the leading end of the insertion portion 14 passes through the attaching hole 13, the operator pushes the leading end of the insertion portion 14 into the attaching hole 13 of the opposed fixing part 12A and causes the leading end of the insertion portion 14 to pierce through the attaching hole 13. As a result of this, as shown in FIG. 4C, the balloon 12 is easily mounted on the leading end of the insertion portion 14.

Figure 4D:
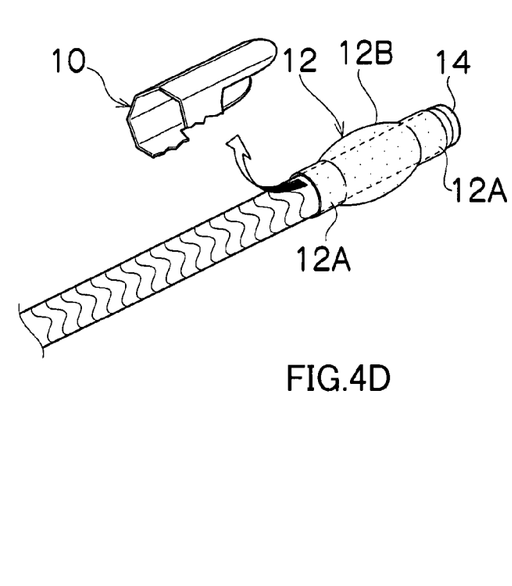

When the balloon 12 is mounted on the leading end of the insertion portion 14, the balloon attaching jig 10 is not necessary anymore. Therefore, the work of removing the balloon attaching jig 10 from the balloon 12 and the leading end of the insertion portion 14 is then performed. That is, as shown in FIG. 4D, after the extraction of the pair of nail members 18 from the attaching hole 13 of the balloon 12, the balloon attaching jig 10 is torn. As a result of this, it is possible to remove the balloon attaching jig 10 from the balloon 12 and the leading end of the insertion portion 14. Because the balloon attaching jig 10 has the cut 21 formed from the end of the tubular body thereof, the balloon attaching jig 10 is easily torn by tearing the balloon attaching jig 10 from this cut.

In contrast, if balloon attaching jig 10 is made of a material incapable of being torn, after the removal of the pair of nail members 18 from the attaching hole 13 of the balloon 12, this balloon attaching jig 10 must be withdrawn from the leading end of the insertion portion 14 by causing the balloon attaching jig 10 to pass by the outer peripheral part of the balloon 12. If the balloon attaching jig 10 is caught by the balloon 12 made of a rubber thin sheet during this withdrawal, the balloon 12 may sometimes be broken.

Therefore, in the case of the balloon 10 of this embodiment made of a tearable material, the tearing of the balloon 10 makes it unnecessary to cause the balloon attaching jig 10 to pass by the outer peripheral part of the balloon 12 and, therefore, it is possible to prevent the balloon 12 from being broken by the balloon attaching jig 10.

Figure 5:
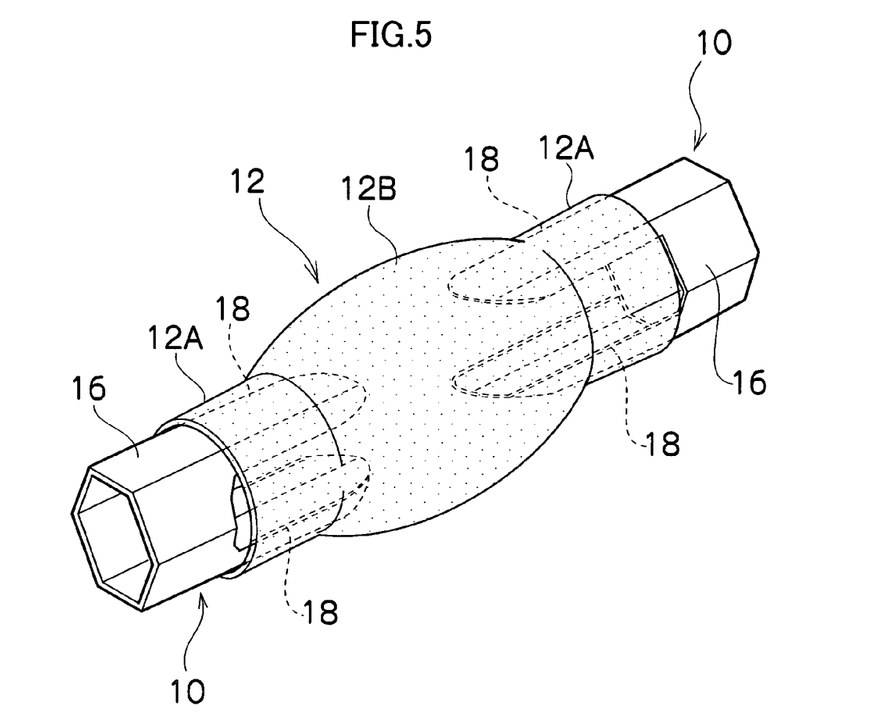
FIG. 5 is a perspective view of the balloon attaching jigs of FIG. 1 that are attached on both sides of a balloon.

Incidentally, in the above-described embodiment, the description was given only of the example in which the balloon attaching jig 10 is attached only to one fixing part 12A of the balloon 12. However, the invention is not limited to this, and as shown in FIG. 5, the balloon attaching jig 10 may be attached also to the other fixing part 12A. In this case, by picking up the nail members 18 with fingers, it is possible to expand the diameter of the two fixing parts 12A and hence it is possible to insert more easily the leading end of the insertion portion 14 into balloon 12.

Figure 6:
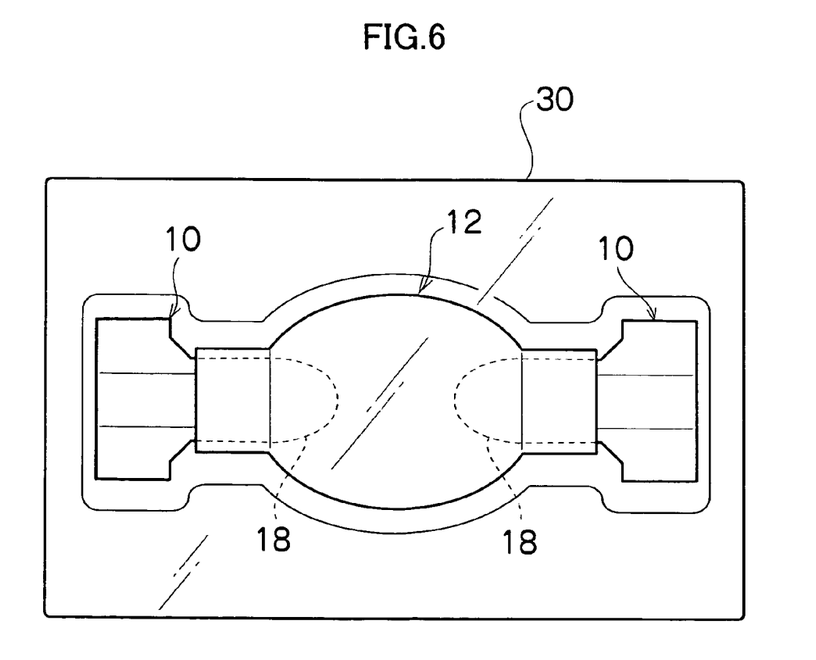
FIG. 6 is a plan view of a container in which the balloon and balloon attaching jigs of FIG. 5 are packaged.
Figure 7:
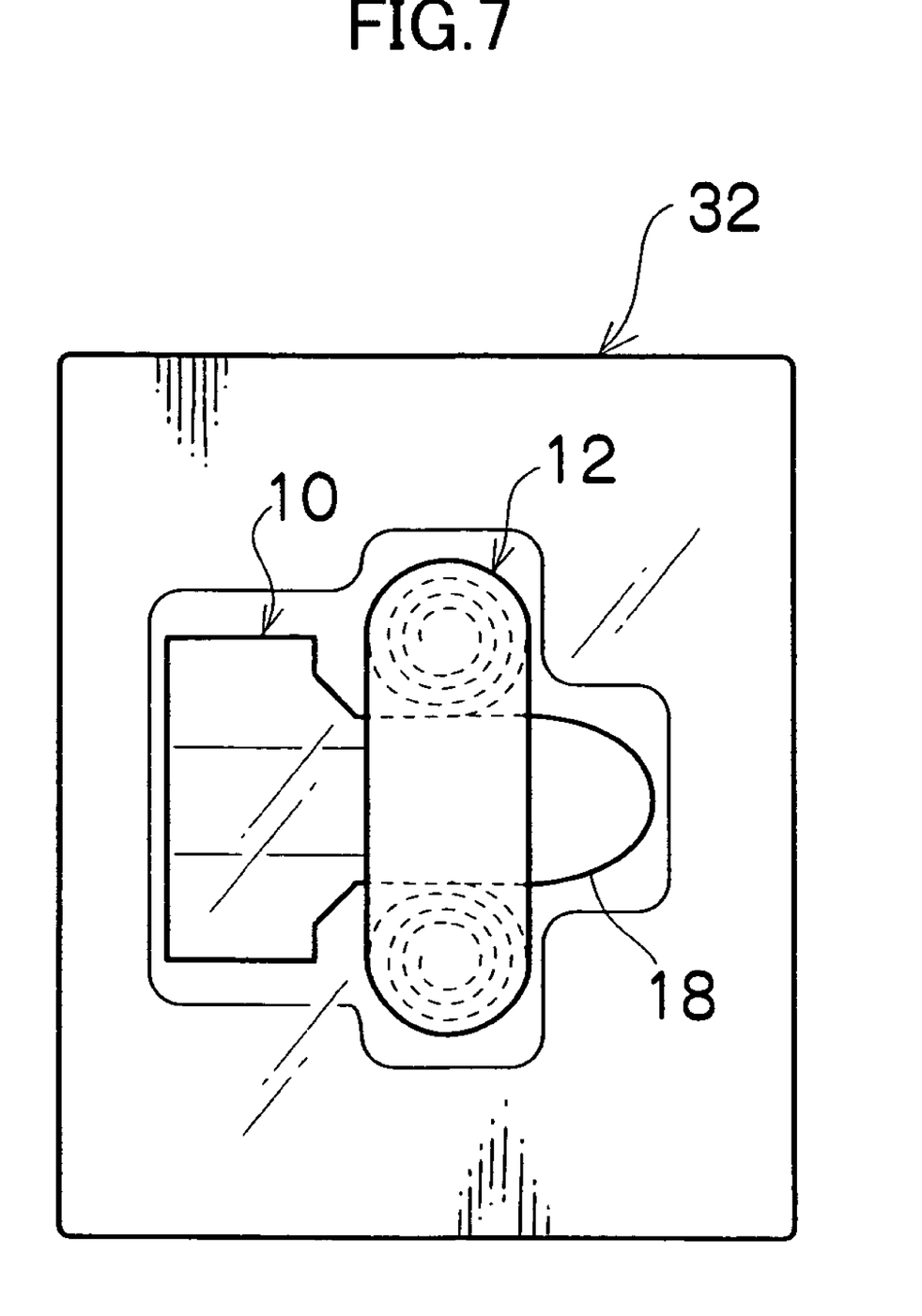
FIG. 7 is a plan view of a container in which a balloon attaching jig is packaged with a balloon wound on nail members of the jig.

FIG. 6 is a plan view of a container 30 in which the balloon 12 and balloon attaching jigs 10 of FIG. 5 are packaged. This container 30 is fabricated from a paper box, a plastic case, etc. and the surface thereof is coated with a transparent body so that the interior can be seen. FIG. 7 shows an example in which the balloon 12 is mounted by being wound around the nail member 18 of the balloon attaching jig 10 shown in FIG. 4B and packaged in a container 32. This container 32 is constructed in the same manner as with the container 30 of FIG. 6. The containers 30, 32 are sterilized and by breaking the containers 30, 32, the balloon 12 and the balloon attaching jig 10 are taken out and the balloon 12 is attached to the insertion portion of the endoscope via the balloon attaching jig 10. Incidentally, the balloon 12 may be a disposable type so that the balloon 12 after use can be disposed by being torn and removed from the insertion portion of the endoscope. In this case, it is possible to save the time and trouble to perform sterilization.

A balloon attaching jig 50 shown in FIGS. 8A to 8D is integrally constituted by a ring member 52 and multiple comb-toothed portions (guide portions) 54. The comb-toothed portion 54 is formed in a protruding manner along the circumferential edge of the ring member 52 to assume a tubular shape. The balloon attaching jig 50 is made of an elastic member of rubber or the like and has a diameter formed by the comb-toothed portions 54 that expands and contracts freely.

Figure 8A:
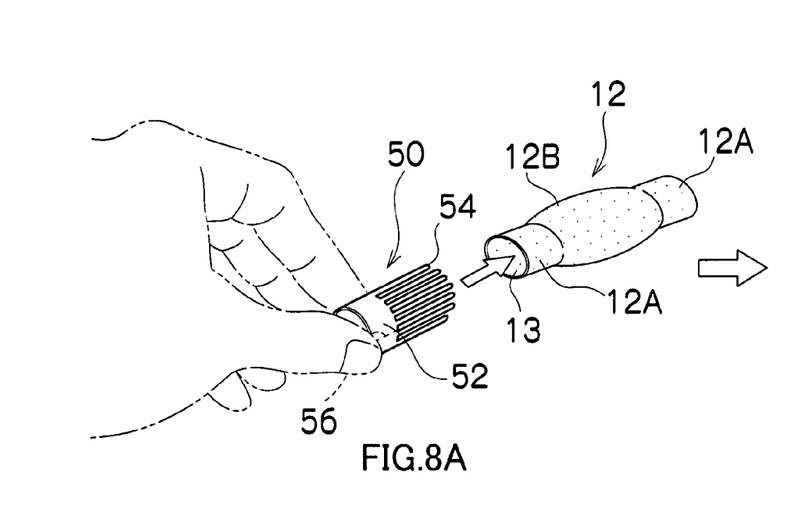
FIGS. 8A, 8B, 8C, and 8D are each an explanatory drawing that shows procedures for attaching a balloon to the leading end of the insertion portion by use of another balloon attaching jig.
Figure 8B:
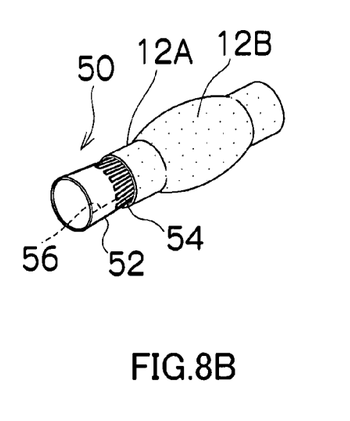

As shown in FIG. 8A, the operator picks up the ring member 52 of the balloon attaching jig 50 with the thumb and forefinger of one hand H and, as shown in FIG. 8B, pushes the comb-toothed portions 54 into the attaching hole 13 of the fixing part 12A of the balloon 12 by a prescribed amount. Incidentally, at this time, the comb-toothed guide portions 54 themselves have not an elastic force large enough to expand the diameter of the attaching hole 13 of the balloon 12. Therefore, at the stage when the balloon attaching jig 50 is mounted on the balloon 12, the comb-toothed guide portions 54 yield under the elastic force of the fixing part 12A of the balloon 12 and is elastically deformed in a tip-narrowed condition.

Figure 8C:
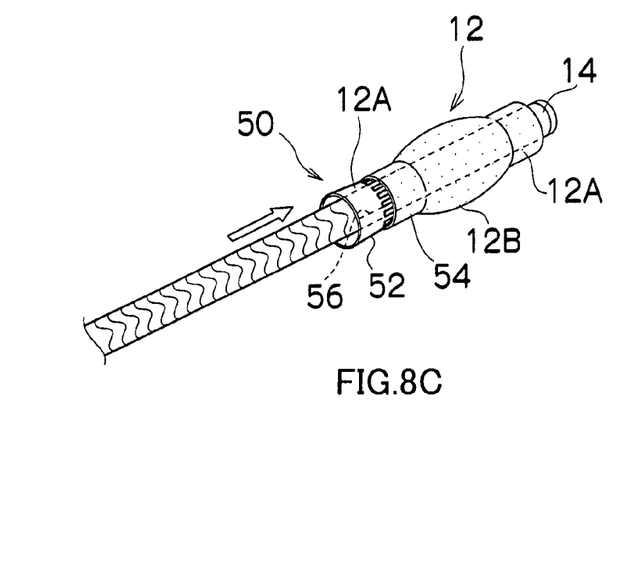

Next, the operator grips the insertion portion with the other hand and inserts the leading end of the insertion portion 14 into the opening of the ring member 52 and pushes in the leading end of the insertion portion 14. When the leading end of the insertion portion 14 is pushed in, the leading end of the insertion portion 14 comes into contact with the comb-toothed guide portions 54 that are in a tip-narrowed condition by the elastic force of the fixing part 12A and receives the resistance of insertion. At this time, a stronger pushing-in force than before is given to the leading end of the insertion portion 14. The comb-toothed guide portions 54 are expanded by this pushing-in force to expand the diameter thereof, with the result that the inside diameter for insertion is expanded and the leading end of the insertion portion 14 is inserted into the attaching hole 13 of the fixing part 12A, with the comb-toothed guide portions 54 serving as guides. And when the leading end of the insertion portion 14 passes through the attaching hole 13, the operator pushes the leading end of the insertion portion 14 into the attaching hole 13 of the opposed fixing part 12A and causes the leading end of the insertion portion 14 to pierce through the attaching hole 13. As a result of this, as shown in FIG. 8C, the balloon 12 is easily mounted on the leading end of the insertion portion 14.

Figure 8D:
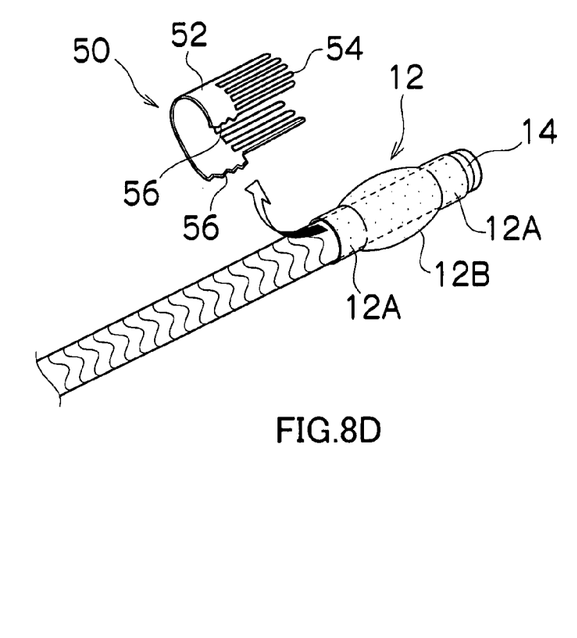

When the balloon 12 is mounted on the leading end of the insertion portion 14, the comb-toothed guide portions 54 of the balloon attaching jig 50 are then extracted from the attaching hole 13 of the balloon 12. After that, as shown in FIG. 8D, the balloon attaching jig 50 is torn. As a result of this, it is possible to remove the balloon attaching jig 50 from the balloon 12 and the leading end of the insertion portion 14. Because the ring member 52 of the balloon attaching jig 50 has a machine-sewed seam 56, the balloon attaching jig 50 can be easily torn by tearing the balloon attaching jig 50 along the machine-sewed seam 56.

Figure 9:
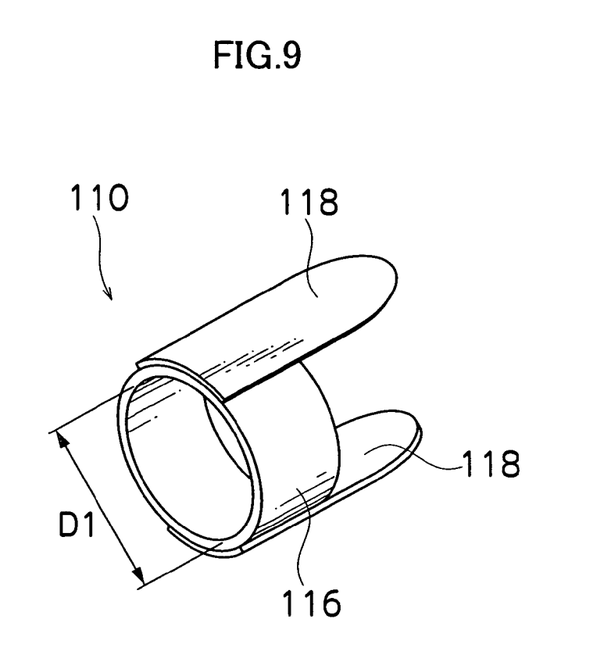
FIG. 9 is a perspective view of a mounting fixture related to the invention.
Figure 10:
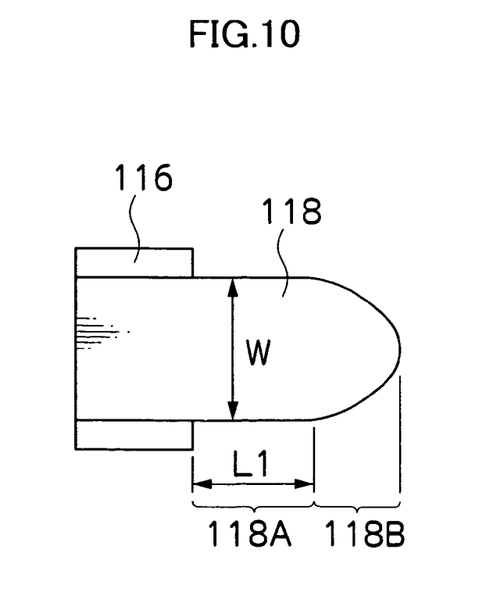
FIG. 10 is a plan view of the mounting fixture of FIG. 9.
Figure 11:
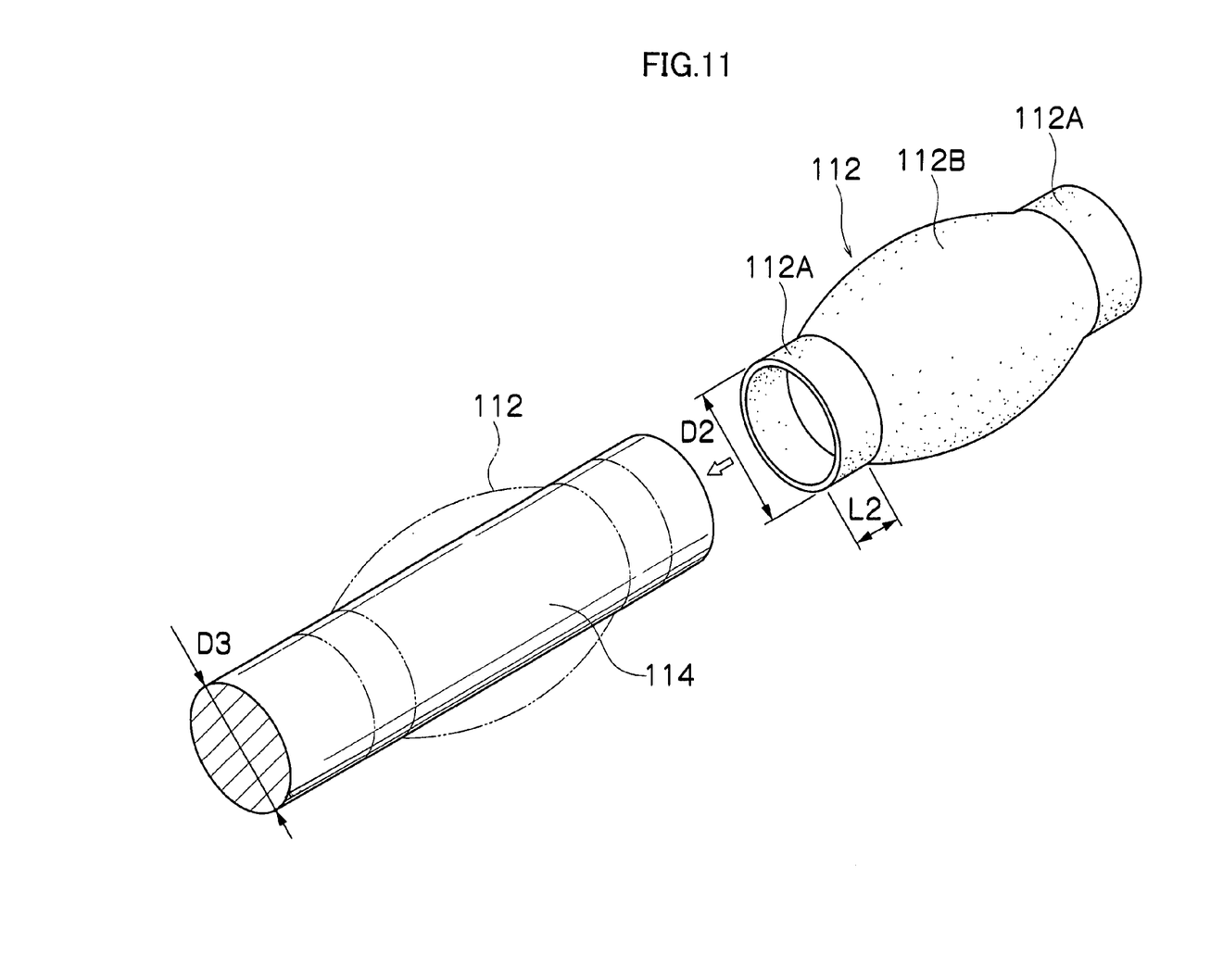
FIG. 11 is a perspective view of a balloon being mounted on the insertion portion by use of the mounting fixture of FIG. 9.

FIG. 9 is a perspective view of another balloon attaching jig 110 related to the invention, and FIG. 10 is a plan view of the mounting fixture 110 of FIG. 9. FIG. 11 is a perspective view of a balloon 112 being mounted on the insertion portion 114 (of an endoscope) by use of the mounting fixture 110 of FIG. 9. Incidentally, in the following embodiment, descriptions will be given of an example in which the balloon 112 is attached to the insertion portion 114. However, the invention is not limited to this and the insertion portion 114 may be mounted on an insertion aid in insertion into a body cavity.

As shown in FIG. 11, the balloon 112 is formed in roughly barreled shape, with both ends being necked, and the balloon 112 has fixing parts (corresponding to attaching holes) 112A at both ends and an inflation part 112B in the middle. The balloon 112 is formed from an elastic body of rubber etc., and formed in such a manner that the inside diameter D2 of the fixing part 112A is smaller than the outside diameter D3 of the insertion portion 114. Therefore, as indicated by the alternate long and two short dashes lines of FIG. 11, when the leading end of the insertion portion 114 is inserted into the balloon 112, the fixing parts 112A of the balloon 112 come into close contact, due to the elastic force thereof, with the outer peripheral surface of the leading end of the insertion portion 114. By winding a thread around the fixing pats 112A or inserting a fixing ring into the fixing pats 112A, the balloon 112 is firmly mounted on the leading end of the insertion portion 114. When air is supplied to the interior of the mounted balloon 112, the inflation part 112B inflates and by sucking the air from the interior, the inflation part 112B sticks to the outer peripheral surface of the leading end of the insertion portion 114. Incidentally, the shape of the balloon 112 is not limited to the above-described example, and for example, a cylindrical balloon or a balloon having only one attaching hole may be used.

The mounting fixtures 110 shown in FIGS. 9 and 10 are jigs that put the insertion portion 114 into the above-described balloon 112 and constituted by a ring member 116 and a pair of nail members 118.

The ring member 116 is formed in such a manner that the inside diameter D1 thereof is a little larger than the outside diameter D3 of the insertion portion 114 of FIG. 11 so that the insertion portion 114 can be inserted into the ring member 116. The ring member 116, which is formed from an elastic body of rubber etc., is easily elastically deformed by application of an external force and can be restored to the original shape by a restoring force larger than the balloon 112.

The pair of nail members 118 is formed from a hard material of plastics etc. and is disposed on the opposed sides at 180 degrees, with the ring member 116 interposed. The pair of nail members 118 is curved along the lines of the shape of the outer periphery of the ring member 116 and the base end portions of the nail members 118 are bonded and fixed to the outer peripheral surface of the ring member 116. For this reason, in the nail members 118, a constant-width portion 118A formed with a constant width W and a tapered portion 118B consecutively provided at the leading end side of the constant-width portion 118A protrude from the ring member 116. The constant-width portion 118A is formed in such a manner that the width W thereof is larger than the outside diameter D3 of the insertion portion (see FIG. 11) 114 and the length L1 thereof is larger than the length L2 of the fixing part 112A of the balloon 112 (see FIG. 11). On the other hand, the tapered portion 118B is formed as a tapered portion having a rounded end so that the tapered portion 118B can be easily inserted into the fixing part 112A of the balloon 112 without damaging the balloon 112.

A method of attaching the balloon 112 by use of the mounting fixture 110 constructed as described above will be described below.

Figure 12:
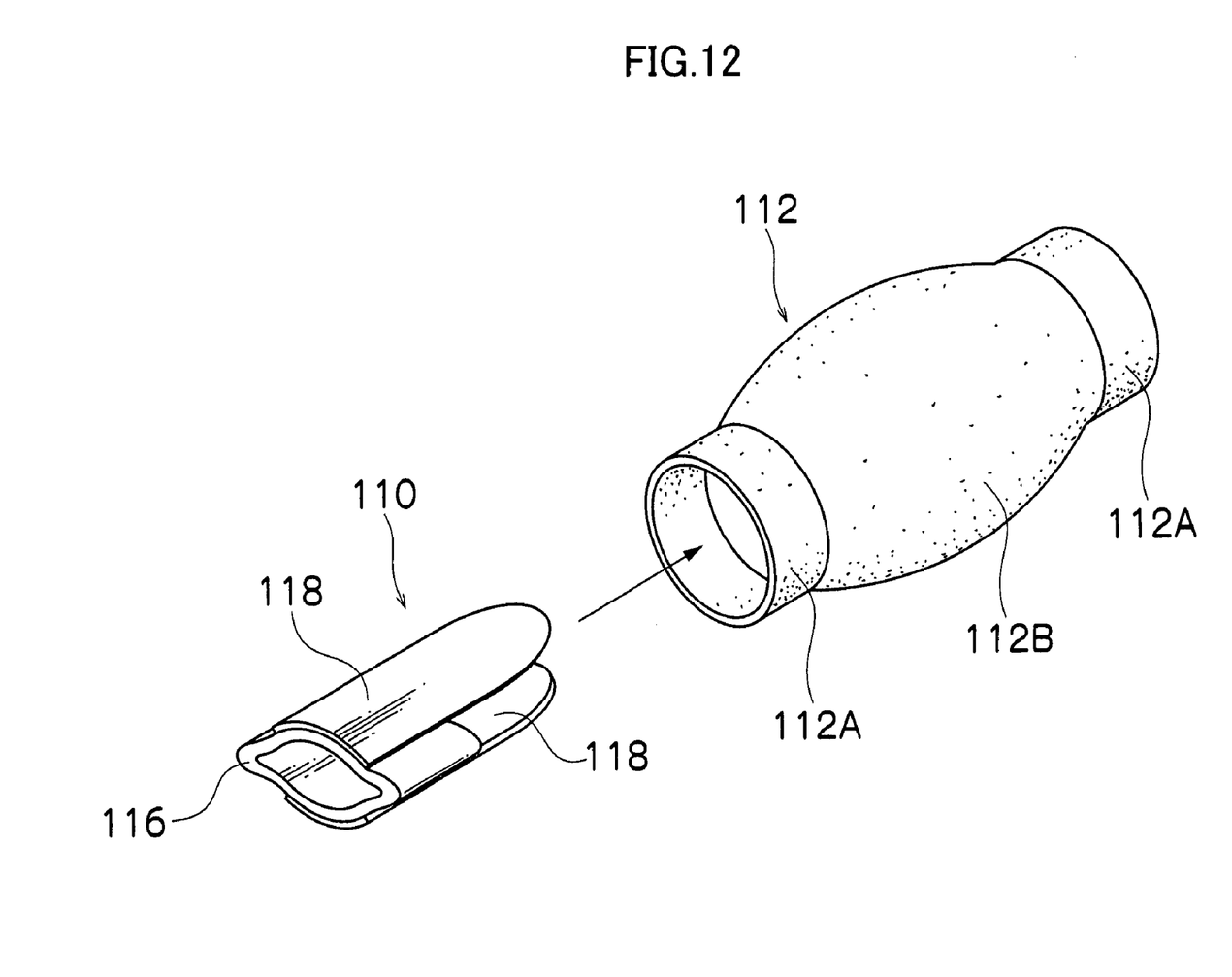
FIG. 12 is a perspective view of a mounting fixture that has elastically deformed a ring member.

The operator puts the thumb and forefinger of one hand on the nail members 118, 118 and depresses the nail members 118 from both outsides. As a result of this, the ring member 116 is elastically deformed as shown in FIG. 12 and the pair of finger members 118 becomes closer to each other.

Next, the operator holds the fixing part 112A of the balloon 112 with the other hand and inserts the pair of nail members 118 into the interior of this fixing part 112A. At this time, because the tapered portion 118B is provided at the leading ends of the nail members 118, it is possible to easily insert the nail member 118 into the interior of the balloon 112. Also, because the interval of the nail members 118 has become narrow throughout from the tapered portion 118B to the constant-width portion 118A, it is possible to easily insert the pair of nail members 118, up to the deep recess of the fixing part 112A of the balloon 112.

Figure 13:
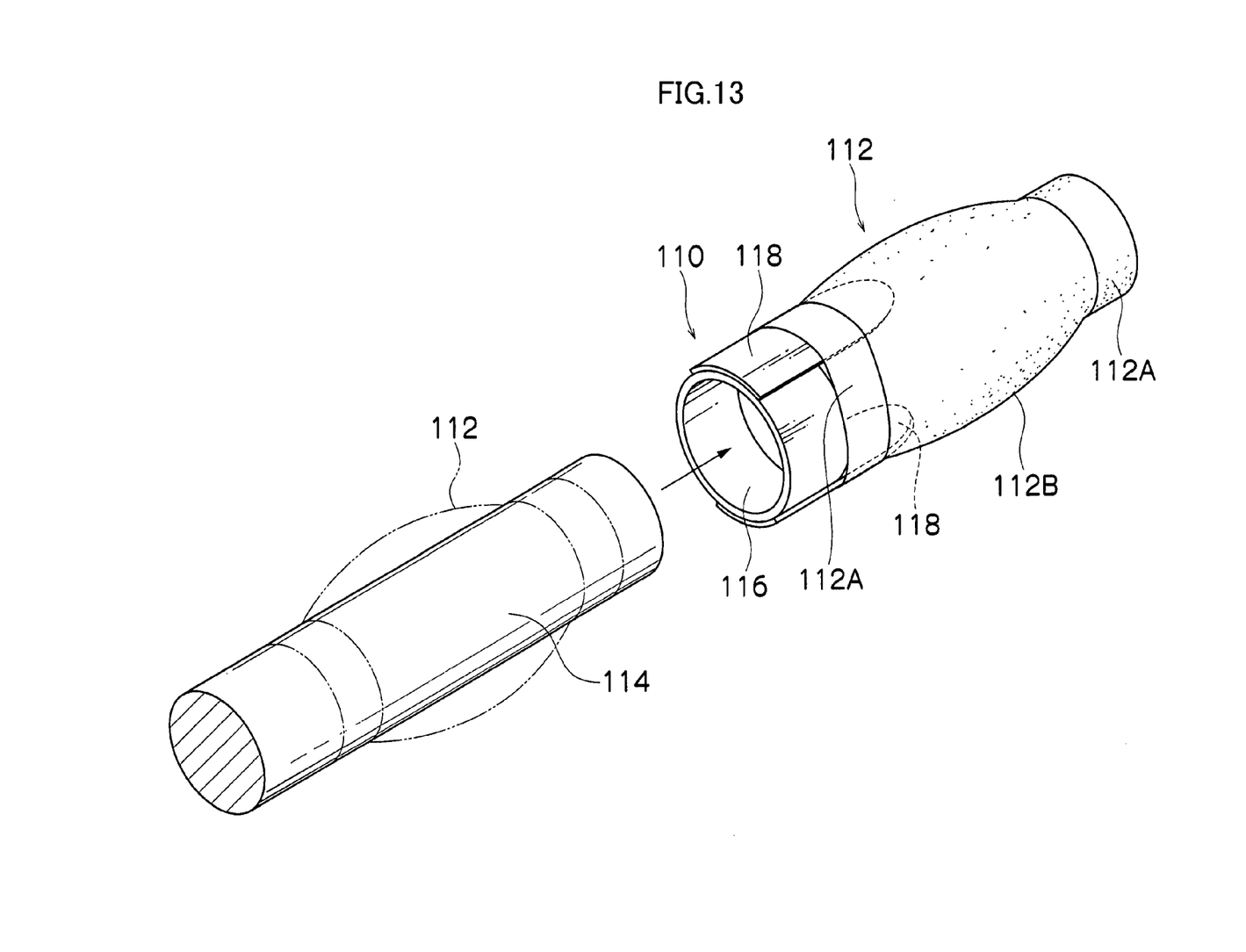
FIG. 13 is a perspective view of a balloon to which a mounting fixture is attached.

After the insertion of the nail members 118 is performed until the fixing part 112A of the balloon 112 completely covers the constant-width portion 118A of the nail member 118, the ring member 116 is restored by weakening the force that depresses the nail members 118. Because the restoring force of the ring member 116 is larger than the restoring force of the balloon 112, the ring member 118 returns to the initial ring shape as shown in FIG. 13 and the fixing part 112A of the balloon 112 is expanded by the pair of nail members 118. Because the width W of the nail members 118 (see FIG. 10) is larger than the outside diameter D3 of the insertion portion 114 (see FIG. 11), the fixing part 112A of the balloon 112 is expanded larger than the insertion portion 114.

Next, while holding the mounting fixture 110 with one hand and holding the insertion portion 114 with the other hand, the operator inserts the insertion portion 114 into the interior of the ring member 116. Because as described above, the fixing part 112A of the balloon 112 is expanded larger than the insertion portion 114, it is possible to easily insert the insertion portion 114 into the interior of the balloon 112.

When the insertion portion 114 is inserted into the balloon 112, the other fixing part 112A is naturally expanded by the insertion of the insertion portion 114. As a result of this, the insertion portion 114 can be inserted into the balloon 112.

And as indicated by the alternate long and two short dashes lines of FIG. 13, upon arrangement of the balloon 112 in a desired mounting position, the operator extracts the mounting fixture 110 from the fixing part 112A of the balloon 112 while holding the inflation part 112B of the balloon 112 or the other fixing part 112A. As a result of this, the fixing parts 112A of the balloon 112 are mounted, due to the elastic force thereof, on the outer peripheral surface of the insertion portion 114 in a close-contact condition. Incidentally, the mounting fixture 110 that has been extracted from the fixing part 112A is withdrawn to the leading end side of the insertion portion 114.

At this time, the balloon 112 is in a deflated condition and, therefore, the ring member 116 will not be caught by the balloon 112.

Thus, according to the mounting fixture 110 of this embodiment, the nail members 118 can be easily inserted into the balloon 112 simply by elastically deforming the ring member 116 and at the same time, the fixing part 112A of the balloon 112 can be easily expanded simply by restoring the ring member 116. Therefore, by inserting the insertion portion 114 into the fixing part 112A expanded by the mounting fixture 110, the insertion portion 114 can be easily inserted into the balloon 112 and the mounting work of the balloon 112 can be easily performed. In particular, because the mounting fixture 110 of this embodiment can be handled with one hand, the fixing part 112A can be expanded by holding the balloon 112 with the other hand and the work can be performed more easily.

Also, according to this embodiment, with the mounting fixture 110 kept attached to the fixing part 112A of the balloon 112, insertion into the insertion portion 114 from the mounting fixture 110 side can be performed. Therefore, the balloon can be attached in a position away from the leading end of the insertion portion 114.

Figure 14:
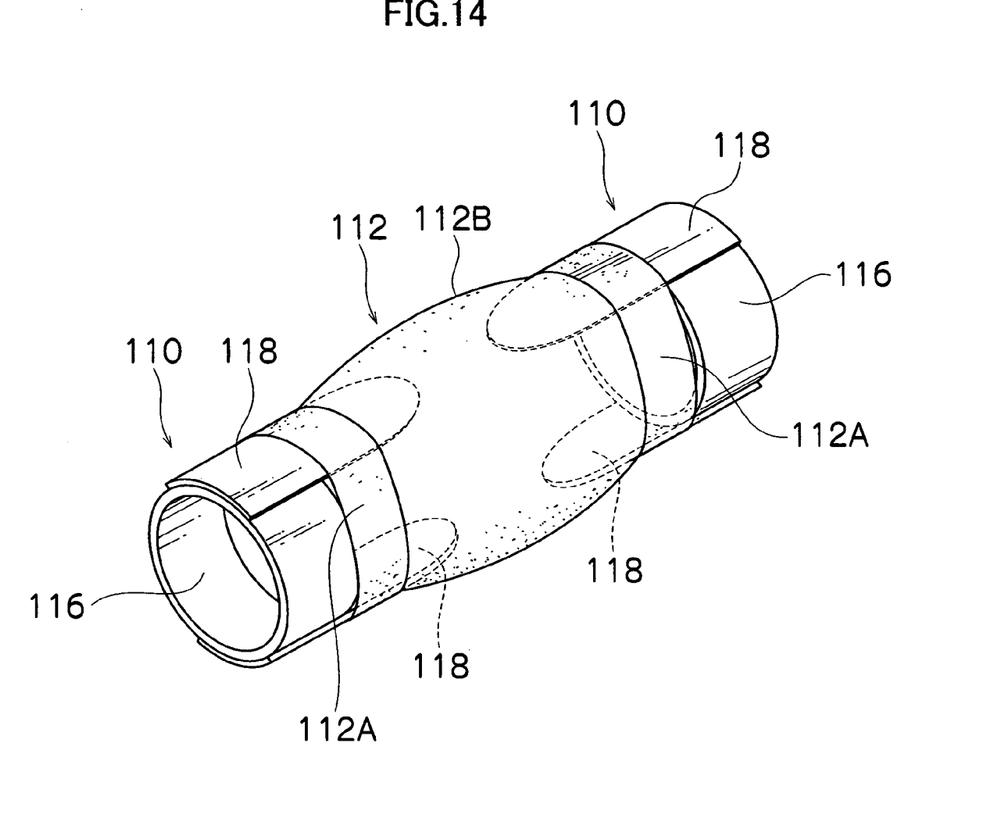
FIG. 14 is a perspective view of a balloon to which mounting fixtures are attached on both sides.

Incidentally, in the above-described embodiment, the mounting fixture 110 is attached only to one fixing part 112A of the balloon 112. However, the invention is not limited to this. As shown in FIG. 14, the mounting fixture 110 may be attached also to the other fixing part 112A. In this case, because the two fixing parts 112A are expanded, it is possible to insert the insertion portion 114 into the balloon 112 more easily.

Figure 15:
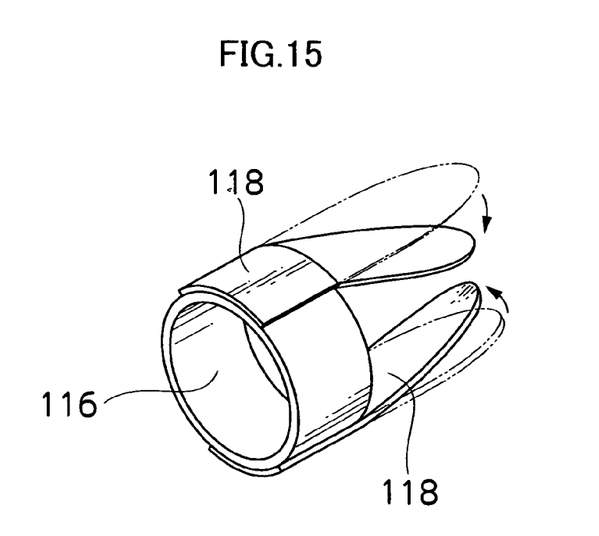
FIG. 15 is a perspective view of a mounting fixture the nail members of which are formed from elastic bodies.

Although in the above-described embodiment, the ring member 116 is formed from an elastic body, the invention is not limited to this. The nail members 118 may be formed from an elastic body and the elastic force thereof may be used. For example, in the mounting fixture 110 shown in FIG. 15, the ring member 116 is made of a hard material such as plastics and the nail members 118 are formed from an elastic body of polyethylene etc. The nail members 118 are elastically deformed so as to deflect inward greatly as indicated by the solid lines in FIG. 15 and become restored so as to be in parallel, as indicated by the alternate long and two short dashes lines of FIG. 15. The restoring force at this time is larger than the restoring force of the balloon 112.

In the mounting fixture 110 constructed as described above, the nail members 118 are inserted into the interior of the fixing part 112A of the balloon 112 (see FIG. 10), with the nail members 118 being depressed from outside and greatly elastically deformed. And by relaxing the depressing pressure on the nail members 118, 118 to cause the nail members 118 to be restored, the fixing part 112A of the balloon 112 is expanded. As a result of this, the insertion portion 114 can be easily inserted into the balloon 112 and the mounting work of the balloon 112 can be easily performed.

Incidentally, in the invention, it is necessary only that at least one of the ring member 116 and the nail members 118 be formed from an elastic member having a larger restoring force than the balloon 112, and the other may be formed from a hard material or an elastic material having a larger restoring force than the balloon 112. Therefore, both the ring member 116 and the nail members 118 may be formed from an elastic member having a larger restoring force than the balloon 112.

What is claimed is:

1. An endoscope and a balloon, including a balloon attaching jig that is used to attach the balloon having an inflation part and a fixing part to an insertion portion of the endoscope or an insertion aid that aids in insertion of the insertion portion into a body cavity by inserting the insertion portion or the insertion aid into an attaching hole of the balloon formed at the fixing part, the jig comprising:
- a ring member having an inside diameter larger than an outside diameter of the insertion portion of the insertion aid;
- a plurality of guide pieces that are integrally formed with the ring member or have a base end portion fixed to the ring member;
- a guide portion that is inserted into the attaching hole of the balloon and into which the insertion portion or the insertion aid is inserted,
- wherein the diameter of the guide portion can expand and contract freely, and
- the plurality of guide pieces are formed longer than the fixing part of the balloon so that a distal end of the guide pieces come to rest within the inflation part when the jig is fully inserted into the attaching hole of the balloon.

2. An endoscope and a balloon, including a jig that is used to attach the balloon having an inflation part and a fixing part to an insertion portion of the endoscope or an insertion aid that aids in insertion of the insertion portion into a body cavity by inserting the insertion portion or the insertion aid into an attaching hole of the balloon formed at the fixing part, the jig comprising:
- a ring member having an inside diameter larger than an outside diameter of the insertion portion or the insertion aid; and
- a plurality of guide pieces that are formed integrally with the ring member or have a base end fixed to the ring member,
- wherein in a state that the guide pieces are inserted into an attaching hole of the balloon, when the insertion portion of the endoscope or the insertion aid is pushed into an opening of the ring member, a diameter formed by the guide pieces is expanded by a pushing-in force generated by pushing-in so that the insertion portion of the endoscope or the insertion aid is inserted into the attaching hole of the balloon, and
- the plurality of guide pieces are formed longer than the fixing part of the balloon so that a distal end of the guide pieces come to rest within the inflation part when the jig is fully inserted into the attaching hole of the balloon.

3. An endoscope and a balloon, including a jig that is used to attach the balloon to an insertion portion of the endoscope or an insertion aid that aids in insertion of the insertion portion into a body cavity by inserting the insertion portion or the insertion aid into an attaching hole of the balloon, the jig comprising:
- a ring member having an inside diameter larger than an outside diameter of an endoscopic insertion portion or an insertion aid; and
- a plurality of guide pieces that have a base end fixed to the ring member,
- wherein at least one of the ring member and the guide pieces is formed from an elastic member having a larger restoring force than the balloon,
- wherein the guide pieces are formed longer than a fixing part of the balloon so that a distal end of the guide pieces come to rest within an inflation part of the balloon when the jig is fully inserted into the attaching hole of the balloon,
- wherein when the guide pieces are inserted into the attaching hole of the balloon while the elastic member is being elastically deformed, the elastic member expands the attaching hole of the balloon from inside by the restoring force, and
- wherein said ring member and said guide pieces are adapted to allow for an air-tight connection to be made between said endoscope insertion portion or said insertion aid and the balloon, when said endoscope insertion portion or said insertion aid is inserted into said ring member and said guide pieces are inserted into the attaching hole of the balloon.

4. A balloon attaching jig of an endoscope that is used to attach a balloon having an inflation part and a fixing part to an insertion portion of an endoscope or an insertion aid that aids in insertion of the insertion portion into a body cavity by inserting the insertion portion or the insertion aid into an attaching hole of the balloon formed at the fixing part, comprising:
- a ring member having an inside diameter larger than an outside diameter of the insertion portion of the insertion aid;
- a plurality of guide pieces that are integrally formed with the ring member or have a base end portion fixed to the ring member;
- a guide portion that is inserted into the attaching hole of the balloon and into which the insertion portion or the insertion aid is inserted,
- wherein the diameter of the guide portion can expand and contract freely, and
- the plurality of guide pieces are formed longer than the fixing part of the balloon so that a distal end of the guide pieces come to rest within the inflation part when the jig is fully inserted into the attaching hole of the balloon,
- wherein the ring member includes acute-angle corners, the corners configured to allow an operator to depress the corners to expand the ring member from a folded condition.

5. A balloon attaching jig of an endoscope that is used to attach a balloon having an inflation part and a fixing part to an insertion portion of an endoscope or an insertion aid that aids in insertion of the insertion portion into a body cavity by inserting the insertion portion or the insertion aid into an attaching hole of the balloon formed at the fixing part, comprising:
- a ring member having an inside diameter larger than an outside diameter of the insertion portion or the insertion aid; and
- a plurality of guide pieces that are formed integrally with the ring member or have a base end fixed to the ring member,
- wherein in a state that the guide pieces are inserted into an attaching hole of the balloon, when the insertion portion of the endoscope or the insertion aid is pushed into an opening of the ring member, a diameter formed by the guide pieces is expanded by a pushing-in force generated by pushing-in so that the insertion portion of the endoscope or the insertion aid is inserted into the attaching hole of the balloon, and
- the plurality of guide pieces are formed longer than the fixing part of the balloon so that a distal end of the guide pieces come to rest within the inflation part when the jig is fully inserted into the attaching hole of the balloon,
- wherein the ring member includes acute-angle corners, the corners configured to allow an operator to depress the corners to expand the ring member from a folded condition.

6. A balloon attaching jig of an endoscope that is used to attach a balloon to an insertion portion of an endoscope or an insertion aid that aids in insertion of the insertion portion into a body cavity by inserting the insertion portion or the insertion aid into an attaching hole of the balloon, comprising:

a ring member having an inside diameter larger than an outside diameter of an endoscopic insertion portion or an insertion aid; and a plurality of guide pieces that have a base end fixed to the ring member, wherein at least one of the ring member and the guide pieces is formed from an elastic member having a larger restoring force than the balloon, wherein the guide pieces are formed longer than a fixing part of the balloon so that a distal end of the guide pieces come to rest within an inflation part of the balloon when the jig is fully inserted into the attaching hole of the balloon, wherein when the guide pieces are inserted into the attaching hole of the balloon while the elastic member is being elastically deformed, the elastic member expands the attaching hole of the balloon from inside by the restoring force, and wherein said ring member and said guide pieces are adapted to allow for an air-tight connection to be made between said endoscope insertion portion or said insertion aid and the balloon, when said endoscope insertion portion or said insertion aid is inserted into said ring member and said guide pieces are inserted into the attaching hole of the balloon wherein the ring member includes acute-angle corners, the corners configured to allow an operator to depress the corners to expand the ring member from a folded condition.

\* \* \* \* \*

UNITED STATES PATENT AND TRADEMARK OFFICE
CERTIFICATE OF CORRECTION

PATENT NO. : 7,591,782 B2
APPLICATION NO. : 11/004866
DATED : September 22, 2009
INVENTOR(S) : Tetsuya Fujikura Page 1 of 1

It is certified that error appears in the above-identified patent and that said Letters Patent is hereby corrected as shown below:

Title Page, Item (73) Assignee: should read
    -- FUJIFILM CORPORATION, Tokyo (JP); SRJ CORPORATION, Tochigi (JP) --

Signed and Sealed this
Twelfth Day of March, 2013

Teresa Stanek Rea
*Acting Director of the United States Patent and Trademark Office*